(12) United States Patent
Horio et al.

(10) Patent No.: US 6,302,314 B1
(45) Date of Patent: Oct. 16, 2001

(54) METHOD FOR EXAMINING BONDED-METAL BY ULTRASONIC EXAMINATION

(75) Inventors: Hirotsugu Horio, Tokai; Hisao Nakase, Anjo, both of (JP)

(73) Assignee: Daido Tokushuko Kabushiki Kaisha, Nagoya (JP)

(*) Notice: Subject to any disclaimer, the term of this patent is extended or adjusted under 35 U.S.C. 154(b) by 0 days.

(21) Appl. No.: 09/224,710

(22) Filed: Dec. 31, 1998

(30) Foreign Application Priority Data

Jan. 16, 1998 (JP) .................................................. 10-020213
Sep. 3, 1998 (JP) .................................................. 10-249243

(51) Int. Cl.⁷ .................................................. B23K 31/12
(52) U.S. Cl. .................................................. 228/103; 228/104
(58) Field of Search .................................... 228/103, 104; 73/599, 588, 582

(56) References Cited

U.S. PATENT DOCUMENTS

| | | | |
|---|---|---|---|
| 4,265,119 | * 5/1981 | Dubetz et al. | 73/588 |
| 4,685,334 | * 8/1987 | Latimer | 73/599 |
| 5,092,176 | * 3/1992 | Buttram et al. | 73/599 |
| 5,329,561 | * 7/1994 | Desruelles | 376/245 |
| 5,408,881 | * 4/1995 | Piche et al. | 73/582 |

FOREIGN PATENT DOCUMENTS

A-58-47252   3/1983   (JP) .

* cited by examiner

*Primary Examiner*—M. Alexandra Elve
(74) *Attorney, Agent, or Firm*—Oliff & Berridge, PLC

(57) ABSTRACT

A method for examining bonded-metal by ultrasonic examination, the method comprising a step of measuring an attenuation amount of an ultrasonic wave, the ultrasonic wave being generated by a sending probe and received by a receiving probe through a bonding interface, the sending probe and the receiving probe being disposed on the bonded-metal with putting the bonding interface therebetween, the bonded-metal being bonded under unknown condition, and a step of examining a bonding property of the bonded-metal based on the attenuation amount, with utilizing a relationship between a bonding property and an attenuation amount for standard metal bonded under known condition measured preliminarily.

9 Claims, 9 Drawing Sheets

METHOD FOR EXAMINING BONDED-METAL BY ULTRASONIC EXAMINATION

BACKGROUND OF THE INVENTION

1. Field of the Invention

The present invention relates to a method for examining bonded-metal by ultrasonic examination, and more particularly, to the method by which the bonding properties such as a bonding temperature, a bonding strength and the like are examined on the basis of an attenuation amount of the ultrasonic wave through a bonding interface of the bonded-metal.

2. Description of Related Art

A method for joining metals together is a process by which pieces of metals are joined together, it can be classified generally into two categories: a metallurgic joining method which gives energy locally to metals to form an atomic bonding therebetween, and a mechanical joining method which use rivets and bolts.

The metallurgic joining method is further classified into a fusion welding method, a pressure welding method, a brazing and soldering method, a diffusion bonding method.

A process of the fusion welding method is as follows. Firstly, bonding faces of base metals are heated to be fusion condition. While heating, if necessary, filler metals may be added therein. The base metals are then bonded together.

A process of the pressure welding is that a high mechanical pressure is applied to bonding faces of metals, the metals are then bonded together. This pressure welding method is classified into a cold pressure welding method, a friction welding method, an explosive welding method, a ultrasonic welding method and a resistance welding method.

A process of the brazing and soldering method is as follows. Firstly, the brazing filler metals are caused to flow into gaps between bonding faces under a fusion condition. Secondly, the metals are caused to solidify, then being bonded together. In this process, the employed brazing filler metals have a lower melting point than the base metals have.

Further, a process of the diffusion bonding method is as follows. Firstly, pieces of metals are caused to contact closely, a pressure is then applied thereto under a temperature of a melting point or less of the metals so as not to produce plastic deformation. Secondly, the metals are bonded with employing atomic diffusion produced on a bonding interface. This diffusion bonding method is classified into a solid-state diffusion bonding method and a liquid phase diffusion welding method. The former is that pieces of metals are directly contacted closely, then causing elements to diffuse under a solid-state. The latter is that insert metals having a lower melting point is put between pieces of metals, then being caused to be fused momentary and solidified by way of isothermal solidification with employing elimination of diffusion of the specified elements in a liquid phase.

The metallurgic joining method such as the diffusion bonding method, different from the mechanical joining method, enables to save material and to cut man-hour, thereby producing a joint having excellent bonding strength, air tightness and pressure tightness. In contrast, a procedure for bonding metals together is irreversible, it is therefore difficult to bond them together repeatedly after separation of the bonding. Further, there is such problem that the bonding properties, such as strength and fracture toughness, vary largely, depending on a type of deficiency of a bonding interface. A lot of factors cause such flaws.

Accordingly, in the case that the metallurgic joining method such as a diffusion bonding method requires high reliability, whether deficiency exists at the bonding interface or not, is examined after bonding. Several nondestructive examinations such as a radiographic testing, a ultrasonic examination, a magnetic particle testing and a liquid penetrant testing can be applied to the bonded-metals. In the case of mass production of the same bonded-metals, from which a part is sampled and a test specimen with a bonding interface is cut off. A destructive examination such as a tensile testing is then carried out.

However, the metallurgic joining method such as a diffusion bonding method accompanies a local heating and/or cooling of metals. Thus, a heat-affected zone with variation both a micro structure and a mechanical property is liable to be produced on vicinity of the bonding interface. Even if deficiency such as flaws, blowholes and bonding defectives is not detected, the bonding properties such as joining strength and fracture toughness may unfortunately be deteriorated.

In such case, destructive examination can be applied to samples produced on a large scale. However, it can not be applied to samples produced on a small scale such as a plant production, thus there is no method for examining the bonding properties of the bonded-metal. Further, the actual bonded-metal includes both deficiency (such as flaws, voids and bonding defectives) and a heat-affected zone. There is also no method for examining the bonding properties of such bonded-metal with achieving high accuracy.

In order to overcome such problem, for example, a procedure for bonding metals together may be standardized by a manufacturer's manual book. However, the bonding properties depend on many requirements such as design of joint, accuracy, cleanliness, a bonding temperature, a holding time, and a bonding pressure. Further, in the case of having no choice but to carry out the bonding procedure out of doors, it is influenced by a weather condition such as a temperature as well as skill of an operator. To use the manufacture's manual book is not enough to achieve high reliability for such bonded-metal which is used for such portion that requires particular high-reliability.

SUMMARY OF THE INVENTION

The present invention has been made in view of the above circumstances and has an object to overcome the above problems and to provide a method for examining bonded-metal by ultrasonic examination, which enables to estimate the bonding properties such as strength and fracture toughness of the metals bonded by way of the metallurgic joining method such as the diffusion welding method, without destructing the bonded-metal.

Another purpose of the present invention is to provide a method for examining bonded-metal by ultrasonic examination, which enables to achieve high-accuracy of estimation.

To achieve the objects and in accordance with the purpose of the present invention, as embodied and broadly described herein, a method for examining bonded-metal by ultrasonic examination, the method comprises a step of measuring an attenuation amount of an ultrasonic wave, the ultrasonic wave being generated by a sending probe and received by a receiving probe through a bonding interface, the sending probe and the receiving probe being disposed on the bonded-metal with putting the bonding interface therebetween, the bonded-metal being bonded under unknown condition, and a step of examining a bonding property of the bonded-metal based on the attenuation amount, with utilizing a relationship between a bonding property and an attenuation amount for standard metal bonded under known condition measured preliminarily.

The attenuation amount of ultrasonic wave through bonded-metal is effected by variation of a bonding property at vicinity of a bonding interface. In the case that the bonding property varies due to heat-history, variation of the bonding property is detected in terms of variation of the attenuation amount of ultrasonic wave through the bonding interface.

By comparing the attenuation amount for actual bonded-metal with the attenuation amount for standard metal bonded under known condition, the bonding property of the actual bonded-metal can be estimated, with utilizing a relationship between a bonding property and an attenuation amount for the standard metal.

Preferably, it may be desirable to select a bonding temperature or a bonding strength as the bonding property. Because, a bonding strength is the most important evaluation item for structures upon which stress act, additionally, a bonding temperature affects exceedingly a bonding strength. Where, the bonding properties mean all properties which affect mechanical properties of bonded-metal except deficiency such as flaws, voids and bonding defectives formed on a bonding interface. Accordingly, follows may also be listed as the bonding properties: the bonding conditions such as a bonding temperature, a cooling rate and a heat-treatment temperature, and mechanical properties such as a bonding strength, a yield strength, hardness, fracture toughness, and the material properties such as composition and a grain size.

Preferably, an ultrasonic wave of a longitudinal wave mode may be adopted for the examination. Because, an attenuation amount of the longitudinal wave through the bonding interface varies largely due to variation of the bonding property, thereby enabling to improve reliability of the examination results.

Preferably, the longitudinal wave may be generated so that an angle of incidence to the bonded-metal may be within a range from 17° to 30°. If an angle of refraction is less than 17°, S-N ratio is lowered with an increase in noise. If the angle of refraction is more than 30°, then degree of contamination of a transverse wave increases. Either of which accompanies deterioration of snesitomety, not being suitable for the ultrasonic examination.

Preferably, a frequency of the longitudinal ultrasonic wave may be within a range from 4 MHz to 10 MHz. If a frequency is less than 4 MHz, then a wave length unfortunately becomes long with a spread in an angle of beam spread, resulting deterioration of directivity. If a frequency is more than 10 MHz, the attenuation unfortunately becomes too steep with a deterioration of snesitomety, not being suitable for the ultrasonic examination.

Preferably, the probes may be rectangular probes having each side within a range from 8 mm to 15 mm long. Comparing a circular probe with a rectangular probe under the same area, a rectangular probe has better both directivity and sensitivity than a circular probe. If a side of a probe is less than 8 mm, then an angle of beam spread becomes wider with a deterioration of directivity. If a side of probe is larger than 15 mm, then a near sound field critical distance becomes longer. Further, strong interference is generated in the near sound field with an increase in noise.

Preferably, the bonded-metal may be made from duplex steel containing two phases or more. In particular, the duplex steel may be duplex stainless steel or precipitation hardening stainless steel based duplex steel. For examples, the duplex stainless steel which austenite having large attenuation of an ultrasonic wave is dispersed into ferritic steel in a ratio of 1:1, the precipitation hardening stainless steel based the above identified duplex stainless steel may be employed as the bonded-metal.

According to the first aspect of the present invention, there is such advantage that the bonding properties such as a bonding temperature and a bonding strength can be estimated without destructing the bonded-metal to be examined.

Further, there is such advantage that accuracy of examination can be improved by employing a longitudinal wave and by optimizing an angle of refraction and a frequency of an ultrasonic wave and a size of a probe. Because a variable range of attenuation which varies with a bonding property becomes large with keeping high snesitomety.

Further, if duplex steel containing two phases or more, such as duplex stainless steel, is applied to the examination object, then variation of a bonding property is remarkably represented as variation of attenuation of an ultrasonic wave. Accordingly, a bonding property can be examined fairly accurately without destructing the bonded-metal.

Referring to the first aspect of the present invention, a bonding temperature and a bonding strength of metals bonded under unknown condition can be estimated with achieving high accuracy, even if a sampling inspection can not be applied. If the present invention is employed for examining a pipe arrangement such as a steel oil well and a chemical plant, then reliability of the bonding process may be improved, thus achieving high industrial applicability.

The second aspect of the present invention, a method for examining bonded-metal by ultrasonic examination, the method comprises a step of detecting whether deficiency exist at a bonding interface or not based on an intensity of reflected ultrasonic wave, the intensity being measured at the time of being received, the ultrasonic wave being generated by a sending probe and received by a receiving probe, the sending probe and the receiving probe being disposed on the bonded-metal so as to be the same side with respect to the bonding interface, the bonded-metal being bonded under unknown condition, a step of measuring an attenuation amount of an ultrasonic wave only for such bonded-metal detected that there is no deficiency, the ultrasonic wave being generated by a sending probe and received by a receiving probe through the bonding interface, the sending probe and the receiving probe being disposed on the bonded-metal with putting the bonding interface therebetween and a step of examining a bonding property of the bonded-metal based on the attenuation amount, with utilizing a relationship between a bonding property and an attenuation amount for standard metal bonded under known condition measured preliminarily.

In the second aspect of the present invention, as similar to the first aspect of the present invention, preferably, it may be desirable to select a bonding temperature or a bonding strength as a bonding property.

Further, preferably, in the case of detecting deficiency, an ultrasonic wave of a transverse wave mode may be used, and in the case of measuring an attenuation amount, a longitudinal wave may be used having a frequency within a range of 4 MHz to 10 MHz. The longitudinal wave may be generated so that an angle of incidence to the bonded-metal may be within a range from 17° to 30°.

Preferably, the probes may be rectangular probes having each side within a range from 8 mm to 15 mm long. And the bonded-metal may be made from duplex steel containing two phases or more.

According to the second aspect of the present invention, there is such advantage that the bonding property such as a bonding temperature and a bonding strength can be estimated without destructing the bonded-metal to be examined.

Further, referring to the second aspect of the present invention, prior to measuring an attenuation amount of an ultrasonic wave, whether deficiency exist at a bonding interface or not is determined by measuring an intensity of an ultrasonic wave reflected by a bonding interface. only for such bonded-metal detected that there is no deficiency, the attenuation amount of an ultrasonic wave is measured. Accordingly, this allows to measure variation of the attenuation amount with achieving high accuracy, thus enabling to improve accuracy for estimating the bonding property.

Further, the third aspect of the present invention, a method for examining bonded-metal by ultrasonic examination, the method comprises a step of detecting whether deficiency exist at a bonding interface or not, based on an intensity of reflected ultrasonic wave, the intensity being measured at the time of being received, the ultrasonic wave being generated by a sending probe and received by a receiving probe, the sending probe and the receiving probe being disposed on the bonded-metal so as to be the same side with respect to the bonding interface, the bonded-metal being bonded under unknown condition, a step of measuring an attenuation amount of an ultrasonic wave, the ultrasonic wave being generated by a sending probe and received by a receiving probe through the bonding interface, the sending probe and the receiving probe being disposed on the bonded-metal with putting the bonding interface therebetween and a step of examining a bonding property of the bonded-metal based on the attenuation amount, with utilizing a relationship between a bonding property and an attenuation amount for standard metal bonded under known condition measured preliminarily, whereby the detection and the measurement being performed simultaneously.

The third aspect of the present invention utilizes high directivity of an ultrasonic wave. That is, if the space between the probes is appropriate, then respective ultrasonic waves sent by a plurality of proves do not interfere each other even if a plurality of probes generate ultrasonic waves simultaneously.

Accordingly, referring to the third aspect of the present invention, it does not take a long time in the ultrasonic examination, thereby allowing to increase efficiency of procedure for bonding metals together.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
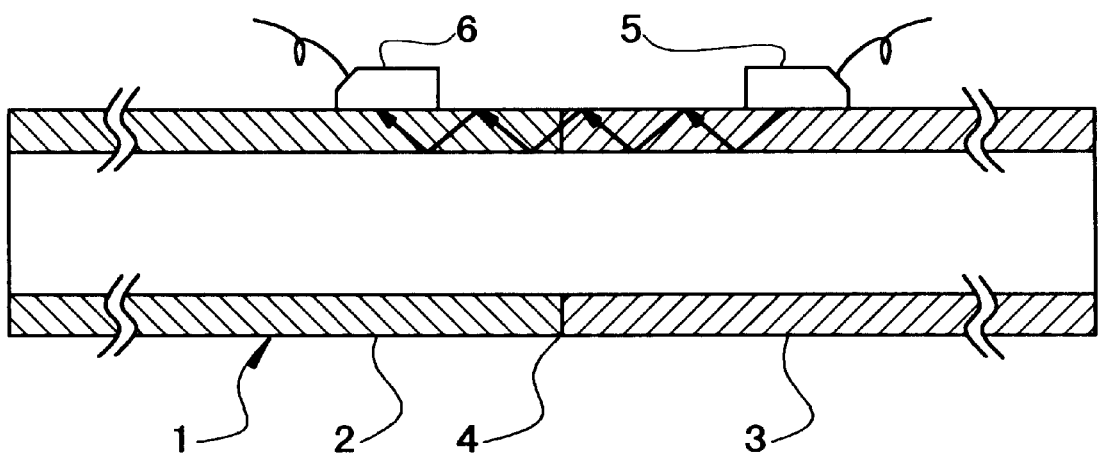
FIG. 1 is a view for illustrating the method for examining bonded-metal by ultrasonic examination of the first preferred embodiment of the present invention.

A detailed description of one preferred embodiment of the present invention will now be given referring to the accompanying drawings. In FIG. 1, a bonded-metal 1 is made of steel pipes 2 and 3 by bonding them at their edges together, an ultrasonic wave sending probe 5 and an ultrasonic wave receiving probe 6 being disposed on the bonded-metal 1 with putting a bonding interface 4 therebetween.

Figure 2:
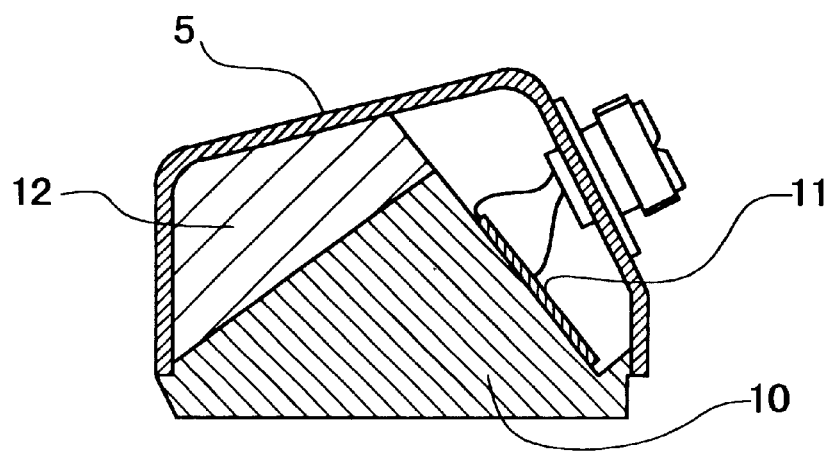
FIG. 2 is a sectional view showing a probe employed in the method of the preferred embodiment of the present invention.

As shown in FIG. 2, the sending probe 5 consists of a wedge 10 made from synthetic resin such as acrylic resin, with which a transducer 11 being put thereon. The transducer 11 is made of a thin plate with electrodes being put on both surfaces. The thin plate is made from piezo-electric material such as crystal, lead niobate, and lead zirconate titanate. Further, a sound absorbing material 12 is put on the wedge 10, thereby allowing to absorb ultrasonic wave reflected by a surface contacting with the bonded-metal 1.

In the case of examining a bonded-metal in the shape of a plate, preferably, a bottom shape of the sending probe 5 may be a flat surface. In the case of examining the bonded-metal 1 having a curved surface, such as steel pipes, preferably, a bottom shape of the sending probe 5 may be a curved surface. The receiving probe 6, which is not shown, is substantially similar to the sending probe 5.

A clearance between the sending probe 5 or the receiving probe 6 and the bonded-metal 1 needs a coupling medium which intervenes therebetween. Since if such clearance exists, then an ultrasonic wave is not sent and received efficiently. Therefore, the coupling medium should be such as to transmit an ultrasonic wave efficiently, and a variety of coupling mediums may be used properly as needed. For examples, water, oil, and glycerine are used as the coupling medium.

In order to receive an ultrasonic wave with the receiving probe 6, which enters into the bonded-metal 1 from the sending probe 5, a positional relationship between the sending probe 5 and the receiving probe 6 should be set accurately. Ultrasonic wave entering into the bonded-metal 1 from the sending probe 5 is propagated therethrough with repeating a total reflection at outer and inner circumferences. Therefore, the receiving probe 6 should be placed at the outer circumferences where an ultrasonic wave after the total reflection at the inner circumferences reaches, or should be placed at the inner circumferences where an ultrasonic wave after the total reflection at the outer circumferences reaches.

Where, one skip is defined as a horizontal distance from the position of the outer circumference where an ultrasonic wave generated by the sending probe 5 placed thereon entering into the bonded-metal 1, to the position of the outer circumference where an ultrasonic wave after one total reflection at the inner circumference reaches. The number of skip where the receiving probe 6 is located may be selected in accordance with a shape of the bonded-metal 1 and a measuring condition. In FIG. 1, the receiving probe 6 is located at the fourth skip from the sending probe 5.

Next, the step of measuring an attenuation amount of an ultrasonic wave through the bonding interface 4 of the bonded-metal 1 by the method of the present invention will be described hereinafter. Firstly, a high-frequency pulse is generated by a synchronous control unit, which is not shown, then transmitted to the sending probe 5 via a high-frequency cable. The high-frequency pulse sent to the sending probe 5 is applied to electrodes which are put on both surfaces of transducer 11, thereby causing the transducer 11 to expand and shrink in a thickness direction, then an ultrasonic wave being generated.

Generated ultrasonic wave enters into the steel pipe 3 via the wedge 10, being propagated toward the steel pipe 2 with repeating the total reflections at inner and outer circumferences. While propagation, the ultrasonic wave is transmitted through the bonding interface 4, then being received by the receiving probe 6 after predetermined number of times of the total reflections.

Received ultrasonic wave is transmitted to the transducer of the receiving probe 6, thereby causing the transducer to expand and shrink in a thickness direction. The mechanical vibration is converted into an electric signal by the transducer, then being sent to a receiving unit of a unillustrated examination unit via the high-frequency cable. The attenuation amount of ultrasonic wave can be calculated based on the ratio of the electric energy received by the receiving probe 6 to the electric energy given to the sending probe 5.

Simultaneously, the depth and lateral scanning is performed by the sending probe 5 and the receiving probe 6 with keeping the fixed probe distance therebetween, such as to correspond to four skips, then the position into which the ultrasonic wave enters varies. Accordingly, all of two-dimensional information over the bonding interface 4 can be obtained. In common, the average of each measurement result is used as an attenuation amount of an ultrasonic wave through the bonding interface 4.

Various kinds of methods such as a zig-zag scanning, a depth scanning and lateral scanning are well known. The method of scanning is not limited to only one method, and may be selected in accordance with a shape of the bonded-metal 1 and the like. In a direction perpendicular to the bonding interface 4, it is enough that a scanning distance is at least 0.5 skip distance in order to scan all over the bonding interface 4. In a direction parallel to the bonding interface 4, it is enough for a bonded-metal in the shape of a plate that a scanning distance is at least a lateral width of the bonding interface 4. And it is enough for a bonded-metal in the shape of a pipe as shown in FIG. 1 that a scanning distance is at least a circumference of the pipe.

Alternatively, a plurality of receiving probes 6 may be disposed on the bonded-metal 1, although the sending probe 5 and the receiving probe 6 are disposed by one piece with putting the bonding interface 4 therebetween. If a plurality of receiving probes 6 is disposed, then attenuation of an ultrasonic wave from one receiving probe 6 to another receiving probe 6 can be measured, accordingly attenuation of an ultrasonic wave through heat-affected zone, which extends laterally with putting the bonding interface 4 therebetween, may be measured in addition to attenuation of an ultrasonic wave through the bonding interface 4.

Alternatively, a plurality of the sending probe 5 and a plurality of the receiving probe 6 may be disposed on the bonded-metal 1. Ultrasonic wave has good directivity, thus if a probe distance between respective sending probes 5, then each ultrasonic wave from each sending probe 5 does not interfere each other. Accordingly, in the case of examining a bonded-metal having wide bonding interface 4, if the sending probe 5 and the receiving probe 6 are disposed by two or more, then a scanning distance becomes short, thereby it does not take a long time for the ultrasonic examination.

Next, the step of estimating the bonding property by the method of the present invention will be described hereinafter. Attenuation of an ultrasonic wave is generated due to scatter of part of an ultrasonic wave being propagated through a bonded-metal. Scatter of an ultrasonic wave is caused by such as grain boundary, internal friction and phase boundary having different acoustic impedance.

Metallurgic joining method accompanies heat treatment on joining process, thereby diffusion, phase transformation, grain growth and the like being generated, thus characteristics of interface vicinity varies before and after joining in some cases. In particular, in the case that the characteristics of interface vicinity is sensitive to heat history, it largely varies due to slight variation of bonding condition, thus being remarkably represented by attenuation variation of an ultrasonic wave through a joining interface.

In the case that mechanical property, as well as the characteristics of interface vicinity, is sensitive to heat history, the mechanical property largely varies due to slight variation of bonding condition. In such case, the relation is uniquely defined by each set of an attenuation variation of an ultrasonic wave and a variation of bonding condition or mechanical property. Accordingly, variation of bonding condition and that of mechanical property can be estimated based on an attenuation amount of an ultrasonic wave.

The method of the present invention can be applied to such phase that the attenuation amount and mechanical properties vary in accordance with variation of the bonding condition, and accuracy of examination may be improved as amount of variation becomes large. For example, in point of a bonding method, a diffusion bonding method is particularly suitable. In the diffusion bonding method, bonding process is performed under approximately 90% degrees of the melting point, thereby causing element to be actively diffused at the bonding interface. Then, the variation of attenuation is remarkably represented in accordance with the variation of bonding condition.

In view of kinds of metal, in the case of an iron based material, for example, a duplex stainless steel which austenite is dispersed into ferritic steel in a ratio of 1:1, and a precipitation hardening stainless steel applying the above identified duplex stainless steel as the base metal are particularly suitable for the metal to be bonded. Austenite has a tendency for crystal grain to be large under a bonding process and the scatter of ultrasonic wave to be large at grain boundary. The reason why metal containing austenite is employed is that variation of characteristics of austenite is remarkably represented by variation of attenuation of the ultrasonic wave.

Ultrasonic examination for bonded-metal will be described hereinafter in detail. Firstly, a standard metal is prepared, which is used in order to examine preliminarily a relationship between a bonding property and an attenuation amount of ultrasonic through the bonding interface. The bonded-metal utilized for preparing the standard metal should be the same metal as actually used bonded-metal. In order to improve estimating accuracy of the bonding property, it is desirable that the shape of the standard metal should be the same as that of actually used bonded-metal.

Next, by changing intentionally the bonding property which should be estimated, the standard metal is bonded under several conditions. In the case of such metal that is employed for structual material upon which stress acts, a bonding strength is the most significant estimating item. The bonding strength is exceedingly affected by a bonding temperature. In such case, by selecting the bonding temperature as the bonding property, then the standard metal may be prepared under several bonding temperatures below or above the commendable bonding temperature.

In the case that the heat treatment after bonding accompanies large variation of characteristics such as strength, fracture toughness and the like of the interface vicinity, the standard metal may be prepared by changing intentionally the heat treatment condition such as a heat-treatment temperature, a holding time, a cooling rate and the like. Listed conditions are considered to be variable at the time of performing the bonding work actually.

Next, as shown in FIG. 1, the ultrasonic examination for the standard metal, prepared by above described procedure, is started. The sending probe 5 and the receiving probe 6 are disposed on the bonded-metal 1 with putting the bonding interface 4 therebetween. Then the depth and lateral scanning is performed by the sending probe 5 and the receiving probe 6 with keeping the fixed probe distance therebetween, and successively attenuation of an ultrasonic wave through the bonding interface 4 is measured in order, then the mean attenuation being calculated.

In the case that the bonding property to be estimated is a bonding temperature, correlation between a bonding temperature and attenuation of an ultrasonic wave may be found by comparing them. In common case, one parameter is defined as the x coordinate axis and the other parameter is defined as the y coordinate axis between them. The measured data are plotted in the coordinates, then a regression analysis being performed. A monomial regression analysis may be adopted in the case that one parameter varies in a linear fashion with the variation of the other parameter. A polynomial regression analysis may be adopted in the case that one parameter varies in a non-linear fashion with the variation of the other parameter.

In the case that the bonding property to be estimated is a tensile strength, after completing the ultrasonic examination for the standard metal, then a destructive examination such as a tensile testing may be performed by using a test specimen sampled from each standard metal. Then, correlation between a tensile strength and attenuation of an ultrasonic wave may be found by a regression analysis in a similar manner as described above.

Then, the acceptance criteria for determining acceptability is prepared based on the found correlation between a bonding property and an attenuation amount of an ultrasonic wave for the standard metal, taking account of dispersion of each measured data. Acceptance criteria may be determined taking account of the required reliability, the required property and the dispersion range of measured attenuation.

Next, the actual bonded-metal being bonded under unknown condition (the bonded-metal to be measured) is examined. Firstly, an attenuation amount of an ultrasonic wave is measured under the same condition as adopted for the standard metal. The bonding property is then estimated, based on the correlation between a bonding property and an attenuation amount of an ultrasonic wave for the standard metal, found by a regression analysis.

For example, in the case of a monomial regression analysis, if a correlation coefficient is approximately 1, then a regression line of attenuation of an ultrasonic wave with respect to the bonding property coincides with a regression line of the bonding property with respect to attenuation of an ultrasonic wave. The bonding property of the bonded-metal to be measured is calculated by substituting the measured attenuation for a regression line of the standard metal. If the calculated bonding property satisfies the predetermined acceptance criteria, then the bonded-metal may be determined to be acceptable, and in the case not satisfying the acceptance criteria, then the bonded-metal may be determined to be unacceptable.

In the case that a coefficient of the obtained regression line of the standard metal is large enough, the interval estimation is made at the predetermined critical rate with utilizing the ultrasonic wave attenuation of the measured bonded-metal. If the estimated bonding-property satisfies the predetermined acceptance criteria, then the bonded-metal may be determined to be acceptable, and in the case not satisfying the acceptance criteria, then the bonded-metal may be determined to be unacceptable. The critical rate may be determined in accordance with reliability required to the bonded-metal.

In the case that the actual bonded-metal is prepared as a manual book, there is high possibility that the characteristics of the bonding interface thereof is approximately the same as that of the standard metal. Accordingly, there is high possibility that the measured attenuation of the ultrasonic wave also satisfies the acceptance criteria.

On the contrary, in the case that the bonding work is not made as a manual book due to inevitability, that is, the work is not made under the predetermined bonding condition, the bonding property varies. Accordingly, attenuation of an ultrasonic wave is out of the acceptance criteria, thus being determined to be unacceptable. For such bonded-metal, where necessary, the bonding zone may be reheated up to the bonding temperature, or nondestructive examination such as radiography may be performed.

Next, examples of the preferred embodiment will be described hereinafter. The method of the present invention is applied to the bonded-metal made of the duplex stainless steel pipes by a liquid phase diffusion bonding.

EXAMPLE 1

Firstly, the preparation of the standard metal was made. The employed metal to be bonded was made of the duplex stainless steel pipes SUS329J1, having an outer diameter of 150 mm and an inner diameter of 120 mm, further being finished so that maximum surface roughness of the bonding interface may be 30μm or less. The insert metal was made from Ni based alloy foil having a melting point of 1040° C. and a thickness of 40 μm.

The insert metal was then inserted between two duplex stainless steel pipes, to which a bonding pressure of 4 MPa was applied in Ar gas under conditions of 1150° C.–1300° C.×60 seconds, thereby two duplex stainless steel pipes being bonded together by the liquid diffusion bonding. As shown in FIG. 1, the sending probe 5 and the receiving probe 6 were then disposed on the resulting bonded-metal 1 with putting the bonding interface 4 therebetween, and attenuation of an ultrasonic wave through the bonding interface 4 (i.e. a relative specific intensity of an ultrasonic wave, hereinbelow referred to as "a relative specific intensity") was measured. The probe distance between the probes 5 and 6 was defined as four skips. A longitudinal wave was employed in the ultrasonic examination.

Figure 3:
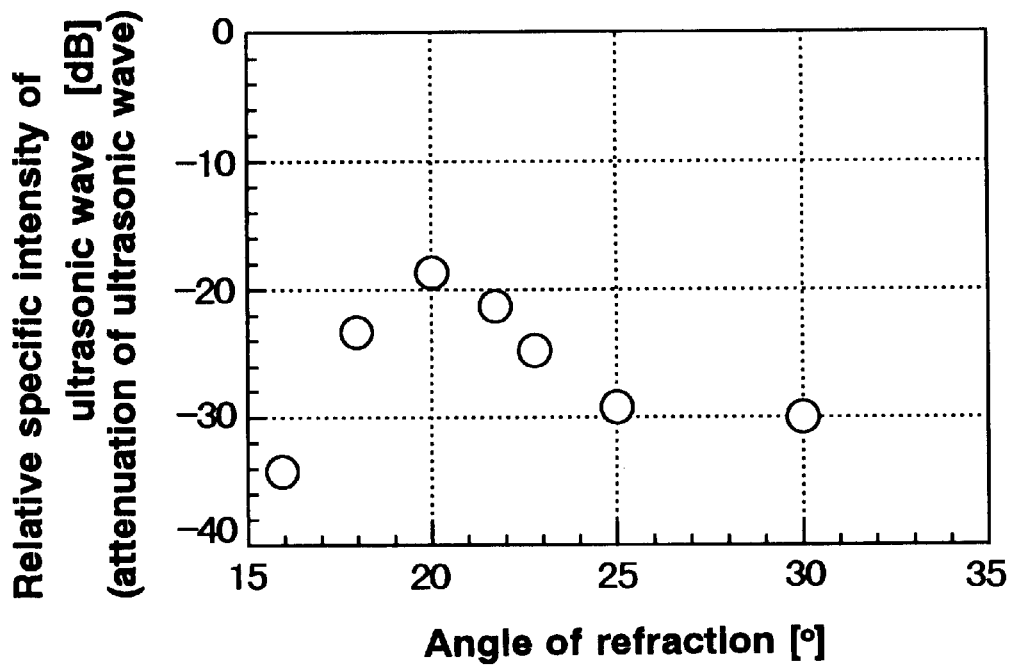
FIG. 3 is a view showing a relationship between an angle of refraction of a longitudinal wave and a relative specific intensity thereof.

By varying angles of refraction, a variation of a relative specific intensity was measured by using the metal bonded under the bonding temperature of 1290° C. The employed probe was a rectangular shape having each side of 10 mm, and the employed ultrasonic wave was of a longitudinal wave mode having a frequency of 5 MHz. As shown in FIG. 3, if an angle of refraction was defined as 20°, then a relative specific intensity reached the maximum value of −19 dB. With a decrease in angle of refraction, a relative specific intensity decreased steeply reaching −34 dB at 16°.

Above 20°, with an increase in angle of refraction, a relative specific intensity decreased reaching −29 dB at 25°. If an angle of refraction was defined as 30°, then a relative specific intensity reached −30 dB. A relative specific intensity at 30° was approximately the same as an intensity at 25°, but there was an increase of noise due to contamination of a transverse wave. Above 30°, contamination of a transverse wave interrupted the measurement.

Figure 4:
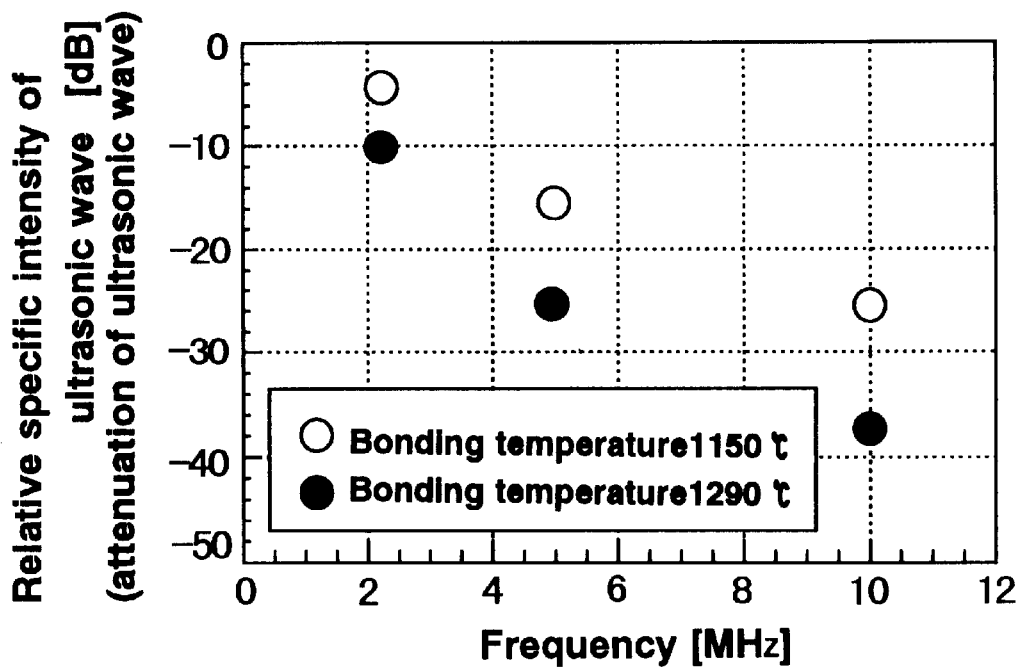
FIG. 4 is a view showing a relationship between a frequency of a longitudinal wave and a relative specific intensity thereof.

By varying a frequency, each variation of each relative specific intensity was measured by using the metals bonded under the bonding temperatures of 1150° C. and 1290° C. respectively. The ultrasonic wave of a longitudinal wave mode was employed. The employed probe was a rectangular shape having each side of 10 mm, and an angle of refraction was defined 20°. As shown in FIG. 4, at a frequency of 2 MHz, a difference between a relative specific intensity of the metal bonded under the bonding temperature of 1150° C. and that of 1290° C. was approximately 6 db.

With an increase of frequency, the difference therebetween was enlarged reaching approximately 11 dB at a frequency of 5 MHz. At a frequency of 10 MHz, the difference therebetween further enlarged to 14 dB, while a relative specific intensity was decreased reaching to approximately −30 dB with a deterioration of snesitometry. If a longitudinal wave having a frequency of 12 MHz or more was employed, the ultrasonic measurement was interrupted due to an increase in noise.

Figure 5:
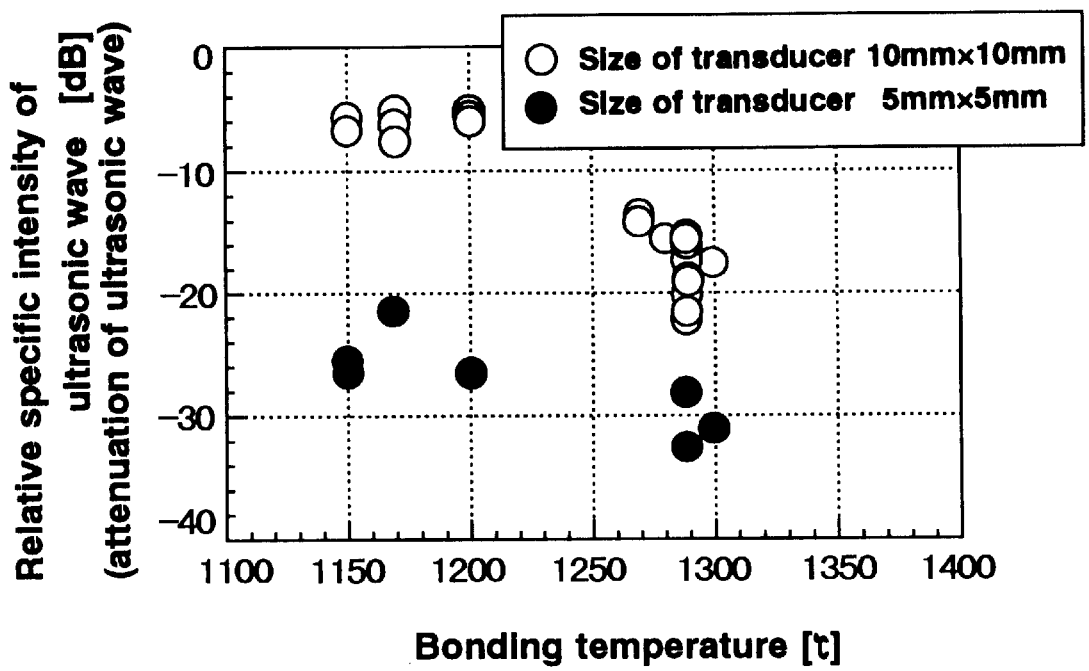
FIG. 5 is a view showing a relationship between a bonding temperature and a relative specific intensity of a longitudinal wave.

By varying a size of a transducer, each variation of each relative specific intensity was measured by using the metals bonded under the bonding temperatures from 1150° C. to 1300° C. The employed ultrasonic wave was of a longitudinal wave mode having a frequency of 5 MHz, and an angle of refraction was defined as 20°. As shown in FIG. 5, if a rectangular transducer having a side of 5 mm was employed, the mean difference between a relative specific intensity of the metal bonded under the bonding temperature of 1150° C. and that of 1300° C. was 10 dB or less.

On the contrary, if a rectangular transducer having a side of 10 mm was employed, the mean difference between a relative specific intensity of the metal bonded under the bonding temperature of 1150° C. and that of 1300° C. was approximately 20 dB. More specifically an amount of variation by using the transducer having a side of 10 mm indicated a value greater than by using the transducer having a side of 5 mm.

As described above, it is clarified that if an angle of refraction, a frequency, and a size of transducer are optimized, then a variation of the bonding temperatures can be detected in terms of a variation of attenuation of an ultrasonic wave, with keeping high-sensitivity of detecting an ultrasonic wave through the bonded-metal.

A monomial regression analysis was made by using results denoted by white points shown in FIG. 5, this case corresponds to employing a rectangular transducer having a side of 10 mm and a longitudinal wave having a wavelength of 5 MHz with an angle of refraction of 20°. Then the following expression was given:

$$\text{Relative specific intensity [dB]} = -0.083 \times \text{Bonding temperature [° C.]} + 91 \quad (1)$$

Figure 6:
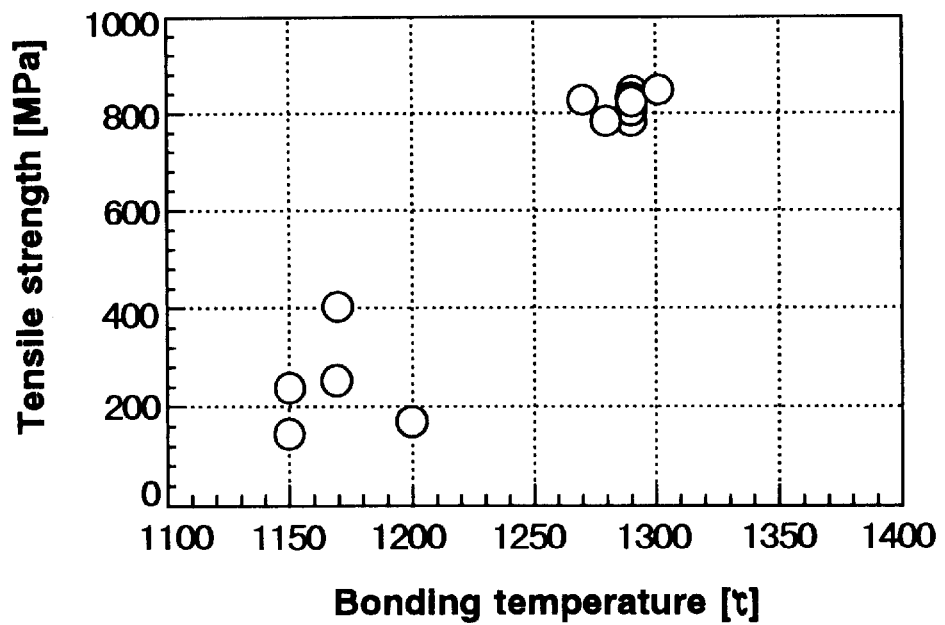
FIG. 6 is a view showing a relationship between a bonding temperature and a tensile strength for the duplex stainless steel pipe, i.e., the standard metal.
Figure 7:
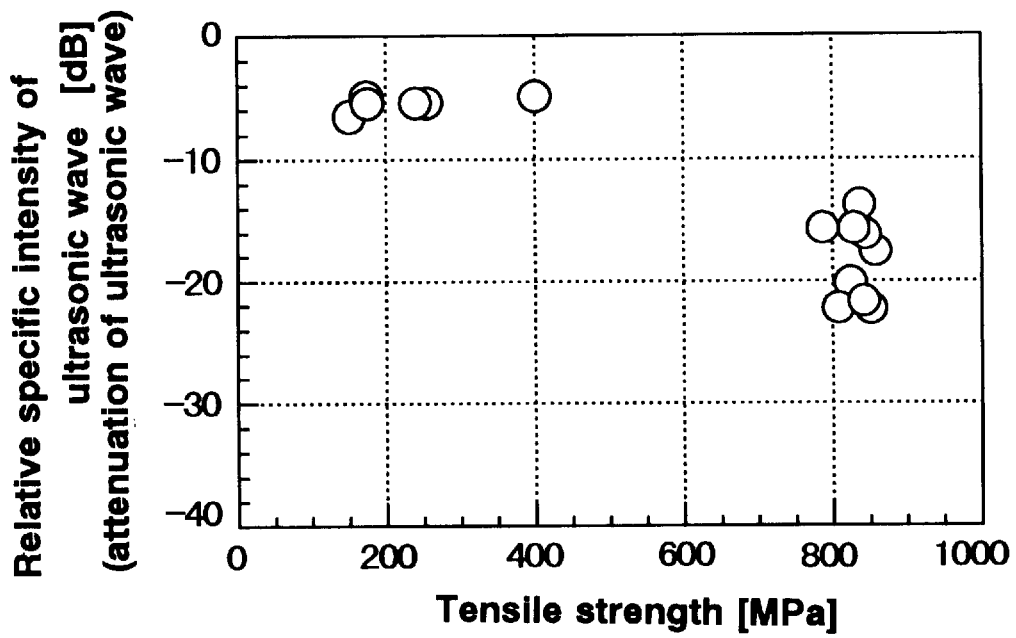
FIG. 7 is a view showing a relationship between a tensile strength and a relative specific intensity of a longitudinal wave for the duplex stainless steel pipe, i.e., the standard metal.

Further, after ultrasonic examination a tensile testing specimen (Japanese Industrial Standard (JIS) Z 3121 No. 4 specimen) was sampled, then a tensile testing being made under a crosshead speed of 1 mm/min. FIG. 6 shows a relationship between a bonding temperature and a resulting tensile strength. As shown in FIG. 6, a tensile strength rose with an increase in bonding temperature. It was clarified that the relation was uniquely defined by each set of a bonding temperature and a tensile strength. As shown in FIG. 7, each relative specific intensity for the standard metal was plotted in the coordinates with respect to each tensile strength. Then a regression analysis was made, the following expression being given:

$$\text{Tensile strength [MPa]} = -40 \times \text{Relative specific intensity [dB]} + 150 \quad (2)$$

By using the expressions (1) and (2), a screening test was carried out in order to confirm whether the bonded-metal having the different bonding-property could be classified or not. Following the same procedures as above mentioned, ten pieces of bonded-metals bonded under the bonding temperature of 1300° C. and ten pieces of bonded-metals bonded under the bonding temperature of 1150° C. were prepared. Prior to the ultrasonic examination, it was confirmed that no deficiency such as flaws and bonding defectives existed.

Next, the estimation of a bonding temperature was performed as following procedures. Firstly, under the condition of hiding history of respective bonded-metals, 100% inspection was carried out by employing a rectangular transducer having a side of 10 mm. The employed ultrasonic wave was of a longitudinal wave mode having a frequency of 5 MHz with an angle of refraction of 20°. The acceptance criteria was defined as −10 dB based on the expression (1); the bonded-metals having a relative specific intensity of −10 dB or more were determined to be unacceptable (corresponding to the bonding temperature of 1200° C. or lower). By the 100% inspection, the metals bonded under a bonding temperature of 1300° C. were all detected.

Next, the estimation of a tensile strength was performed as following procedures. Firstly, the measured attenuation of an ultrasonic wave were substituted for the expression (2), thereby obtaining each tensile strength. The tensile strength of the metal bonded under a bonding temperatures of 1300° C. was 826 MPa, and that bonded under a bonding temperature of 1150° C. was 328 MPa. Further, each test specimen was sampled from the resulting steel pipes bonded under the bonding temperatures of 1300° C. and 1150° C. respectively, then each tensile strength being measured. The results were 835 MPa and 360 MPa, respectively. The results was in good agreement with the estimation based on the expression (2).

EXAMPLE 2

Following the same procedure as in Example 1, the duplex stainless steel pipes were bonded under a different bonding temperatures. Then, an attenuation amount of an ultrasonic wave through the bonding interface 4 was measured by using an ultrasonic wave of a transverse wave mode. The employed probe was a rectangular probe having each side of 10 mm.

Figure 8:
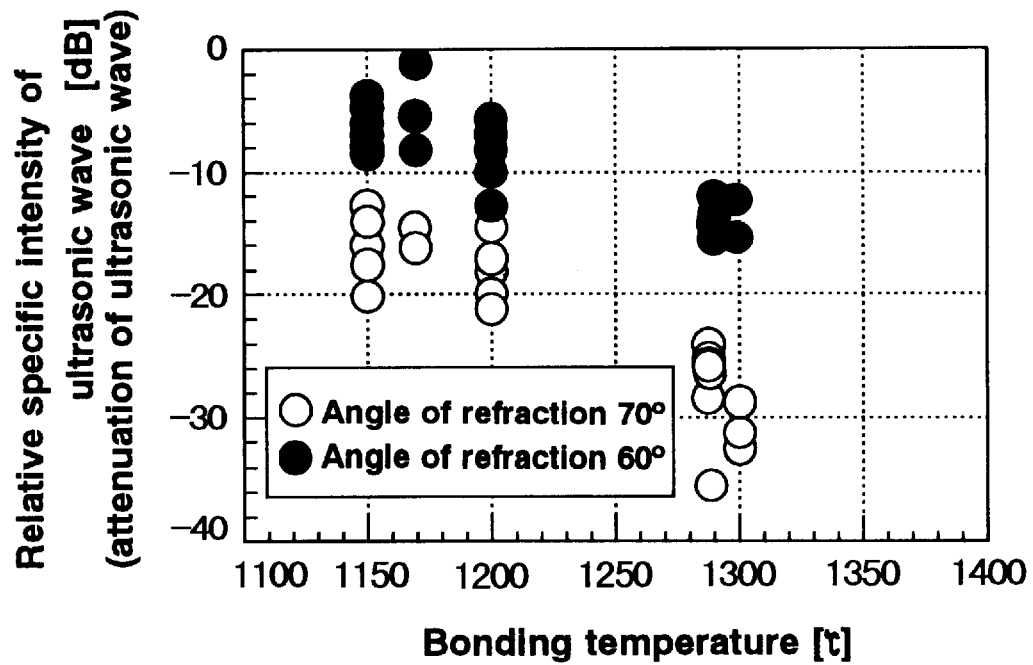
FIG. 8 is a view showing a relationship between a bonding temperature and a relative specific intensity of a transverse wave.

Firstly, a frequency of an ultrasonic wave was defined as 5 MHz, then a transverse wave was generated so that an angle of refraction might be several kinds of values. As shown in FIG. 8, if an angle of refraction was defined as 60°, the mean difference between a relative specific intensity of the metal bonded under the bonding temperature of 1150° C. and that of 1300° C. was approximately 10 dB. On the contrary, if an angle of refraction was defined as 70°, the mean difference therebetween increased to approximately 15 dB.

Figure 9:
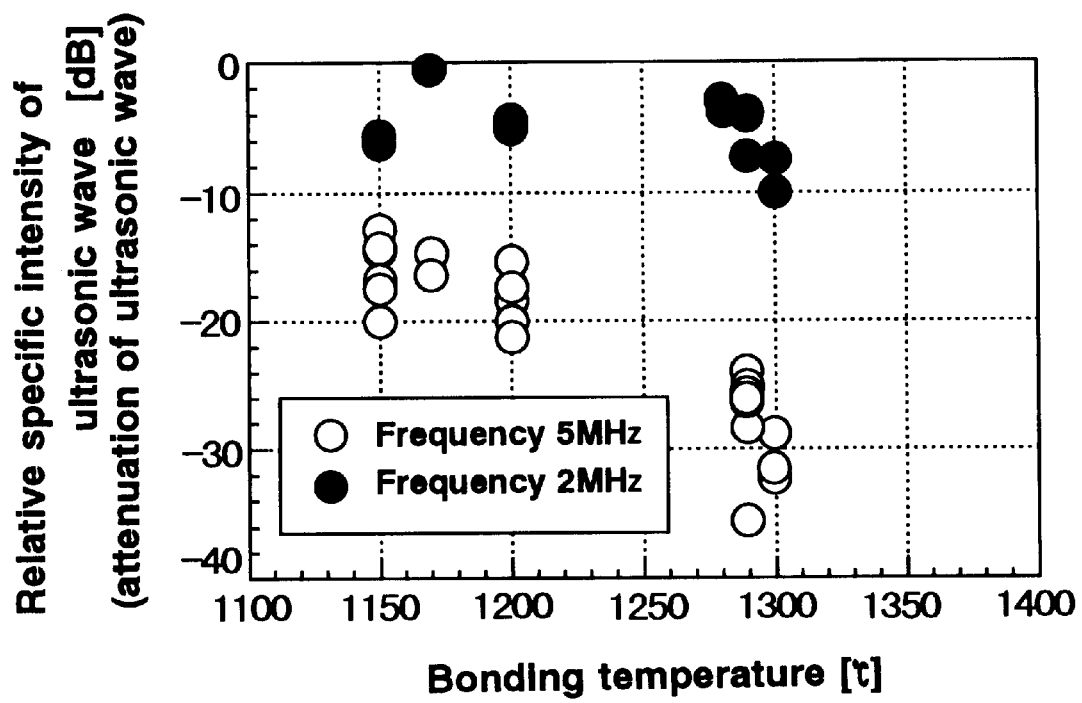
FIG. 9 is a view showing a relationship between a bonding temperature and a relative specific intensity of a transverse wave.

Further, by using a transverse wave having a different frequency, a relative specific intensity was measured with defining an angle of refraction as 70°. As shown in FIG. 9, under a frequency of 2 MHz, a relative specific intensity varied slightly with an increase in bonding temperature. Under a frequency of 5 MHz, the mean difference of a relative specific intensity of the metal bonded under a bonding temperature of 1150° C. and that of 1300° C. was increased to approximately 15 dB.

In addition, comparing white points shown in FIG. 5 with white points shown in FIG. 9, concerning dispersion of a relative specific intensity of the metal bonded under the bonding temperatures of 1150° C. and 1200° C., the dispersion examined under a longitudinal wave is smaller than under a transverse wave. Further, if a longitudinal wave is employed, then the difference between the lower limit at 1150° C. or 1200° C. and the upper limit at 1290° C. increases. Accordingly, FIGS. 5 and 9 indicate that results obtained under a longitudinal wave is more reliable than under a transverse wave.

As far as the examination conditions is appropriate, however, a transverse wave can be employed. And a variation of bonding property can be detected in terms of a variation of attenuation of an ultrasonic wave through a bonding interface, thereby enabling to estimate a bonding property of a bonded-metal having unknown history.

Next, the method for examining bonded-metal by ultrasonic examination of the second preferred embodiment of the present invention will be described hereinafter. The method comprises the step of detecting whether deficiency exist or not, the step of measuring an attenuation amount, and the step of examining a bonding property. The step of detecting whether deficiency exist or not utilizes a reflected wave. This step substitutes for the liquid penetrant testing and X-ray radiography in the first preferred embodiment. The step of measuring an attenuation amount and the step of examining a bonding property are substantially similar to the first preferred embodiment.

Figure 10:
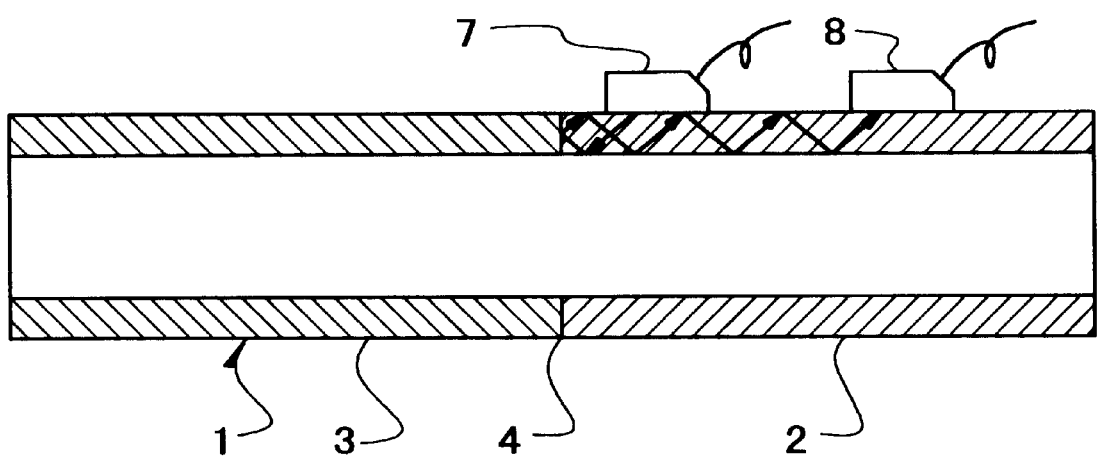
FIG. 10 is a view for illustrating the step for detecting deficiency of the second preferred embodiment of the present invention.

FIG. 10 is a view showing schematic construction of the step of detecting whether deficiency exist or not. Parts in the first preferred embodiment corresponding to parts in the second preferred embodiment carry the same reference numerals. In FIG. 10, the bonded-metal 1 is prepared by bonding the steel pipes 2 and 3 at their ends. On one side of the bonding interface 4, both a sending probe 7 and a receiving probe 8 are disposed. The sending probe 7 generates the ultrasonic wave. The ultrasonic wave is reflected by the bonding interface 4, then the receiving probe 8 receives the reflected ultrasonic wave. The sending probe 7 and the receiving probe 8 are substantially similar to the sending probe 5 and the receiving probe 6, respectively, thus will not be described in detail.

Where, in order to receive the reflected ultrasonic wave, the positional relationship between the sending probe 7 and the receiving probe 8 should be set accurately. The positional relationship therebetween may be determined by similar manner as the first preferred embodiment, thus will not be described in detail.

As shown in FIG. 10, in this second preferred embodiment, the receiving probe 8 is disposed on the third skip from the first point where the reflected ultrasonic wave firstly reaches.

Next, the method of detecting whether deficiency exist or not on the bonding interface 4 by using the reflected ultrasonic wave will be described hereinafter. As similar to the first preferred embodiment, a high-frequency pulse is generated, then being sent to the receiving probe 7 to produce an ultrasonic wave.

Generated ultrasonic wave enters into the steel pipe 2 via the wedge 10, reaching to the bonding interface 4 after one total reflection at an inner circumference. If no deficiency exists on the bonding interface 4, into which the ultrasonic wave enters. If deficiency such as flaws and voids exist on the bonding interface 4, from which the ultrasonic wave is reflected, then reaching to an outer circumference thereof. The ultrasonic wave is received by the receiving probe 8 after propagation through the steel pipe 2 with repeating the total reflections at the inner and outer circumferences.

The received ultrasonic wave is transmitted to the transducer of the receiving probe 8, thereby causing the transducer to expand and shrink in a thickness direction. The mechanical vibration is converted into an electric signal by the transducer, being sent to a receiving unit of a unillustrated examination unit via a high-frequency cable. An intensity of the reflected ultrasonic wave can be calculated based on a level of the electric energy received by the receiving probe 8.

Simultaneously, the depth and lateral scanning is performed by the sending probe 7 and the receiving probe 8 with keeping the fixed probe distance therebetween (for example, three skips), then the position into which the ultrasonic wave enters varies. Thereby, whether the deficiency exist or not on the bonding interface 4 can be examined. As similar to the first preferred embodiment, various kinds of scanning methods can be utilized. Further, the scanning distance may also be determined as the first preferred embodiment.

If an intensity of the reflected ultrasonic wave is noise-echo level, then it is determined that no deficiency exist on the bonding interface 4. Then, the succeeding step of examining bonding property is started.

On the contrary, if an intensity of the reflected ultrasonic wave is over a noise-echo level, then there is a high possibility that deficiency exist on the bonding interface 4. Then, other nondestructive examination is made with discontinuing the ultrasonic examination.

In addition, in the step of detecting deficiency, the ultrasonic wave of a transverse wave mode may be employed. Alternatively, in the case of the bonded-metal 1 made from such metal as to have large attenuation of an ultrasonic wave, the ultrasonic wave of a longitudinal wave mode may be employed.

An angle of refraction and a frequency of an ultrasonic wave entering into the steel pipe 2 from the sending probe 7 and sizes of the sending probe 7 and the receiving probe 8 may be determined and optimized in accordance with a shape and characteristics of the bonded-metal 1 to be measured. In FIG. 10, there is shown the step of detecting deficiency, which uses two angle probes. Alternatively, a single probe technique which causes an ultrasonic wave to generate from the sending probe 7 with aiming directly at deficiency, then receiving the reflected wave with the sending probe 7 may be utilized for detecting deficiency.

Further, two or more pieces of the sending probes 7 and the receiving probes 8 may be disposed respectively. The ultrasonic wave has good directivity, thus if a probe distance is appropriate, then each ultrasonic wave from each sending probe 7 does not interfere each other. Accordingly, in the case of detecting deficiency of a bonded-metal having wide area of the bonding interface 4, if the sending probe 5 and the receiving probe 6 are disposed by two or more respectively, then it is possible to cause a scanning distance to be short. Further, it does note take a long time to perform the examination.

Figure 11:
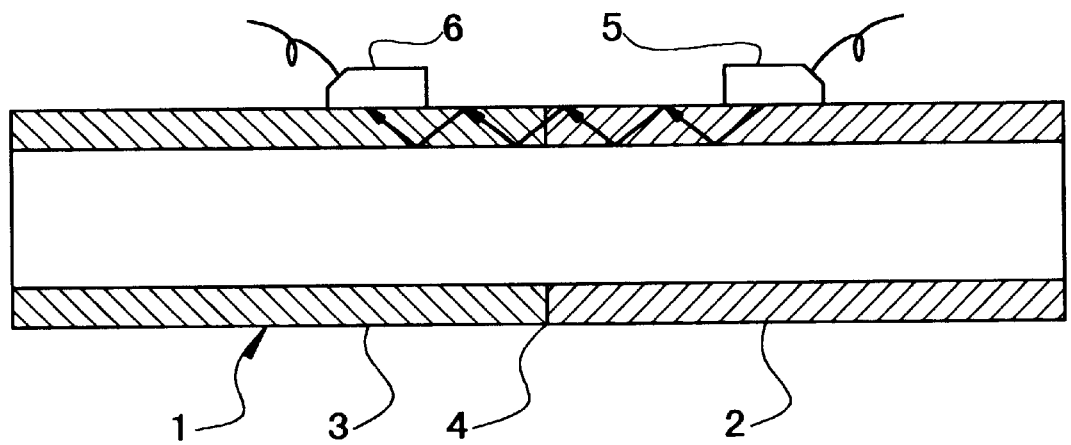
FIG. 11 is a view for illustrating the step for measuring an attenuation amount of an ultrasonic wave of the second preferred embodiment of the present invention.

Next, the step of measuring an attenuation amount will be described hereinafter. The step of measuring an attenuation amount is substantially similar to the method employed in the first preferred embodiment, thus will not be described in detail. FIG. 11 shows the schematic construction of the step of measuring an attenuation amount of the second preferred embodiment. The sending probe 7 and the receiving probe 8 are disposed on the bonded-metal 1 with putting the bonding interface 4 therebetween. In this step, the bonded-metal 1 is determined that there is no deficiency on the bonding interface 4 by the step of detecting deficiency.

Next, the step of examining a bonding property is performed. The step of examining a bonding property is substantially similar to the first preferred embodiment, thus will not be described.

According to the second preferred embodiment, prior to measuring an attenuation amount of ultrasonic wave, whether deficiency exist or not is determined. Thereby an increase in attenuation due to deficiency is not measured in the step of examination. Accordingly, such case can be avoided that the bonded-metal 1 having deficiency is determined to be acceptable by mistake. Since an attenuation amount of an ultrasonic wave is measured accurately, accuracy for estimating the bonding property is improved.

Next, the concrete procedure of the method for examining bonded-metal by ultrasonic examination of the second preferred embodiment of the present invention will be described hereinafter. Firstly, the standard metal is prepared following the same procedure as the first preferred embodiment in order to obtain preliminarily a relationship between a bonding property and an attenuation amount of an ultrasonic wave through the bonding interface. The details of the preparation is substantially similar to that of the first preferred embodiment, thus will not be described.

Next, after confirming that no deficiency exist on the bonding interface 4 by the step of detecting deficiency or other nondestructive examination, then the sending probe 5 and the receiving probe 6 are disposed on the standard metal with putting the bonding interface 4 therebetween as shown in FIG. 11. And the depth and lateral scanning is performed by the sending probe 5 and the receiving probe 6 with keeping the fixed probe distance therebetween. While the scanning, the attenuation amount of ultrasonic wave through the bonding interface 4 is measured successively, then the mean average thereof being calculated.

In the case that the bonding property to be estimated is a bonding condition such as a bonding temperature, the measured attenuation of the ultrasonic wave is compared with a bonding condition (the bonding temperature), thereby the correlation therebetween being found. Based on the correlation, a regression analysis such as a monomial regression analysis and a polynomial regression analysis is performed.

In the case that the bonding property to be estimated is a mechanical property such as a tensile strength, after completing the ultrasonic examination for the standard metal, then the destructive examination such as tensile test may be performed by using a test specimen sampled from each standard metal. The correlation between a tensile strength and an attenuation amount is then found by a regression analysis.

And based on the obtained correlation, the acceptance criteria for determining acceptability is prepared, taking account of dispersion of each measured data, following the same procedures as the first preferred embodiment.

Next, as shown in FIG. 10, the sending probe 7 and the receiving probe 8 are disposed on the same side with respect to the bonding interface 4 of the actual bonded-metal, the bonding property of which is unknown (referred to as "unknown bonded-metal"). Successively, an intensity of a reflected wave is measured.

If an intensity of the reflected ultrasonic wave is noise-echo level, then it is determined that no deficiency exist on the bonding interface 4. Next, as shown in FIG. 11, the sending probe 7 and the receiving probe 8 are disposed on the unknown bonded-metal with putting the bonding interface 4 therebetween. Then an attenuation amount of an ultrasonic wave is measured under the same condition as the standard metal. Successively, the measured attenuation of the ultrasonic wave is compared with the attenuation for the standard metal, thereby the correlation therebetween being found based on a regression analysis. Based on the obtained correlation, the bonding property of the unknown bonded-metal is estimated. The method of estimation of the bonding property may be substantially similar to above mentioned method employed in the first preferred embodiment. The measured attenuation is substituted for the correlation found by a regression analysis. Thereby a bonding property of the unknown bonded-metal is estimated and determined to be acceptable or unacceptable.

Next, an example of the preferred embodiment will be described hereinafter. The method of the present invention is applied to the bonded-metal made of the duplex stainless steel pipes by way of a liquid phase diffusion bonding.

EXAMPLE 3

Firstly, the standard metals prepared in Example 1 were employed in Example 3. In addition, the several standard metals as the Comparative examples were prepared by the same procedure as in Example 1.

In the step of detecting deficiency, as shown in FIG. 10, the sending probe 7 and the receiving probe 8 are disposed on one side with respect to the bonding interface 4, then an intensity of an ultrasonic wave reflected by the bonding interface 4 was measured. A transverse wave mode was employed.

Next, in the step of measuring an attenuation amount, all bonded-metals prepared by the same procedure as in Example 1 were examined as follows. As shown in FIG. 11, the sending probe 7 and the receiving probe 8 are disposed on the bonded-metal 1 with putting the bonding interface 4 therebetween, then an attenuation amount of an ultrasonic wave through the bonding interface 4 (a relative specific intensity) was measured. In addition, a rectangular probe having each side of 10 mm, a transducer of which is made from lead zirconate titanate, is adopted as the sending probe 7 and the receiving probe 8. Further, the employed ultrasonic wave was of a longitudinal wave mode having a frequency of 5 MHz. The ultrasonic wave was generated so that an angle of refraction may be 20°. The probe distance between the sending probe 7 and the receiving probe 8 was defined as four skips, the same as the Example 1.

Figure 12:
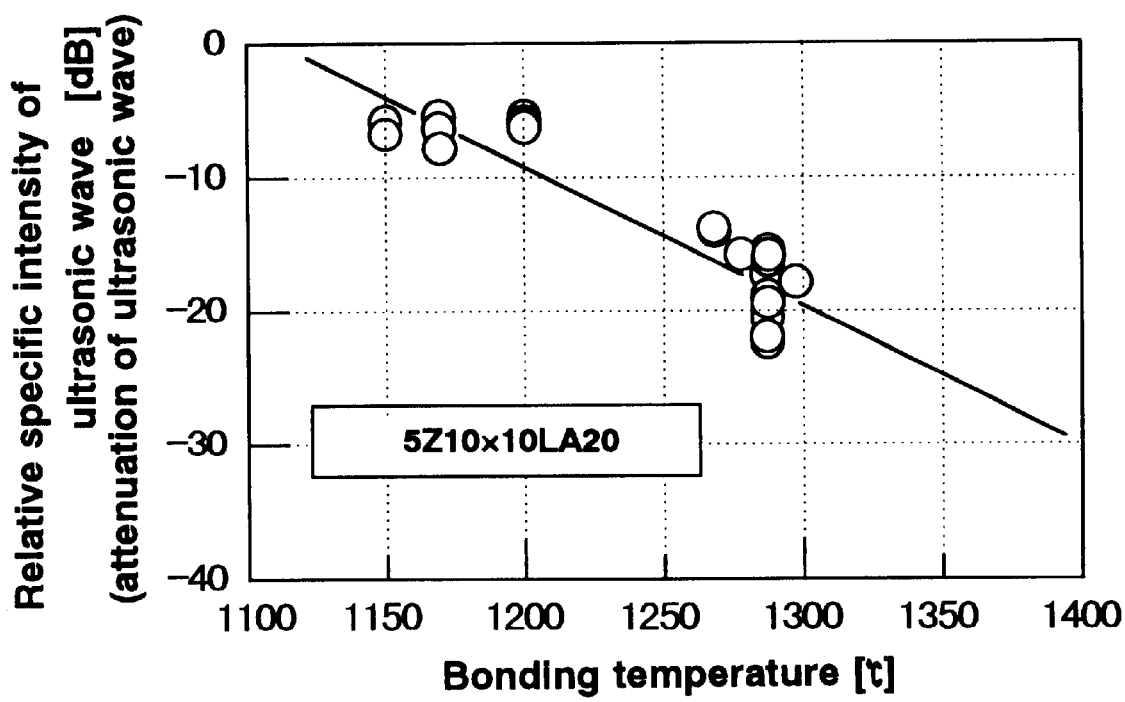
FIG. 12 is a view showing a relationship between a bonding temperature and a relative specific intensity for the bonded-metal for which detecting deficiency has been made.
Figure 13:
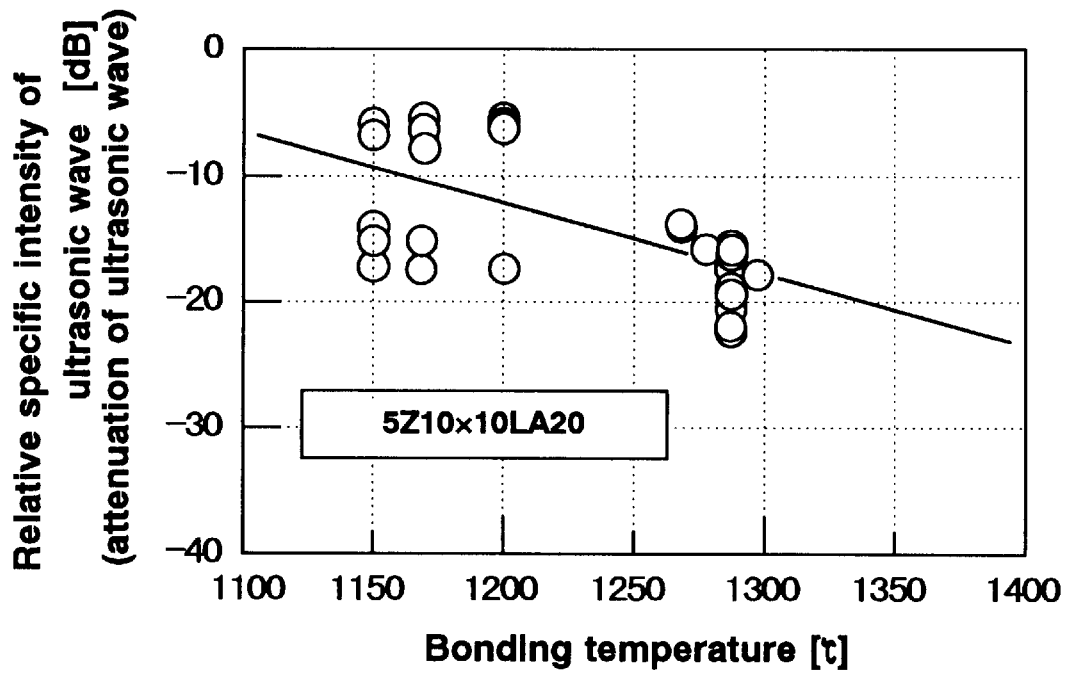
FIG. 13 is a view showing a relationship between a bonding temperature and a relative specific intensity for the bonded-metal for which detecting deficiency has not been made.

The obtained relationships between a bonding temperature and an attenuation amount of an ultrasonic wave through the bonding interface 4 (a relative specific intensity) are shown in FIGS. 12 and 13. FIG. 12 shows the relationship for the acceptable bonded-metals of which an intensity of reflected wave was determined to be a noise-echo level. FIG. 13 shows the relationship for all bonded-metals.

Next, a correlation between a bonding temperature and a relative specific intensity was found. A correlation coefficient for the bonded-metals shown in FIG. 12 was −0.92, thus indicating a strong correlation. On the contrary, a correlation coefficient for the bonded-metals shown in FIG. 13 was −0.66, thus indicating a weak correlation. Accordingly, if the acceptance criteria is prepared by using the bonded-metals of which an intensity of reflected ultrasonic wave is determined to be a noise-echo level in order to estimate a bonding property such as a bonding temperature, then the acceptance criteria achieves high reliability. The result of a monomial regression for the bonded-metals shown in FIG. 12 was given by the expression (1). In Example 3, the expression (1) was adopted as the acceptance criteria in order to estimate a bonding temperature.

Figure 14:
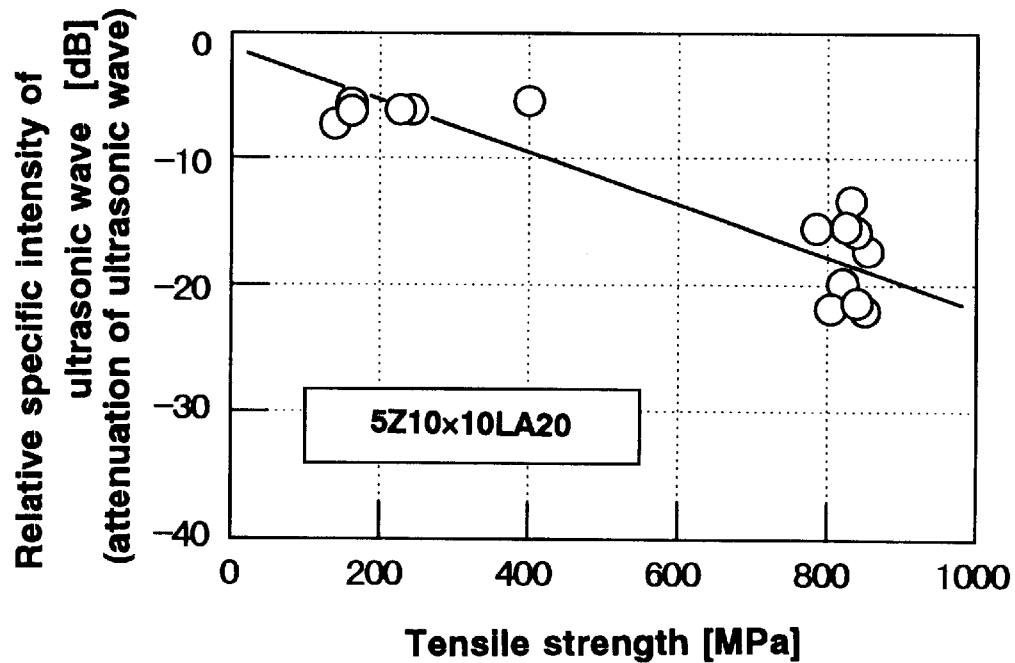
FIG. 14 is a view showing a relationship between a tensile strength and a relative specific intensity for the bonded-metal for which detecting deficiency has been made.
Figure 15:
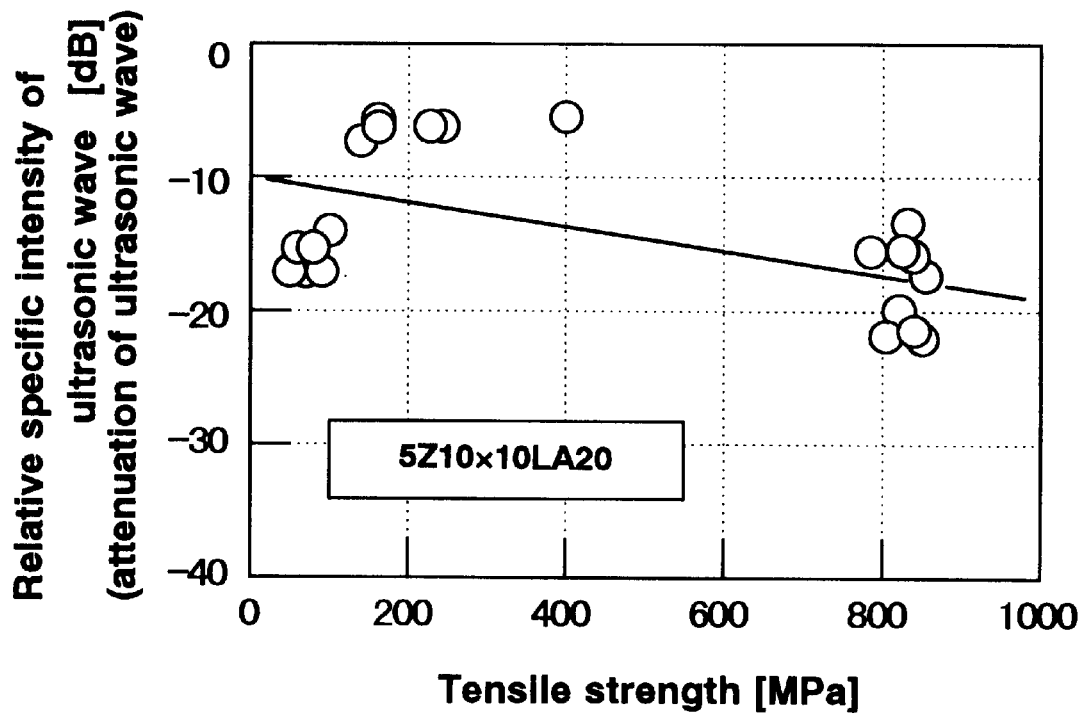
FIG. 15 is a view showing a relationship between a tensile strength and a relative specific intensity for the bonded-metal for which detecting deficiency has not been made.

Next, respective tensile testing specimens (Japanese Industrial Standard (JIS) Z 3121 No. 4 specimen) were sampled from all of the obtained bonded-metals, then a tensile testing being carried out under a crosshead speed of 1 mm/min. FIGS. 14 and 15 show the obtained relationships between a bonding temperature and an attenuation amount of ultrasonic wave through the bonding interface 4 (a relative specific intensity).

In addition, FIG. 14 shows the relationship only for the acceptable bonded-metals of which an intensity of reflected wave to be a noise-echo level. FIG. 15 shows the relationship for all bonded-metals.

Next, a correlation between a tensile strength and a relative specific intensity was found. A correlation coefficient for the bonded-metals shown in FIG. 14 was −0.91, thus indicating a strong correlation. On the contrary, a correlation coefficient for the bonded-metal shown in FIG. 15 was −0.53, thus indicating a weak correlation. Accordingly, if the acceptance criteria is prepared by using the bonded-metals of which an intensity of reflected ultrasonic wave determined to be a noise-echo level in order to estimate the bonding property such as a tensile strength, then the acceptance criteria achieves high reliability. A result of a monomial regression for the bonded-metals shown in FIG. 14 is given by the expression (2). In Example 3, the expression (2) was adopted as the acceptance criteria in order to estimate a tensile strength.

In addition, it was confirmed that a broken-out section of the tensile testing specimen included a non-bonded part, which was sampled from bonded-metals having an intensity level over a noise-echo level. Therefore, deterioration of a correlation coefficient shown in FIGS. 13 and 15 is due to involving such data having an increased attenuation rather than usual.

Next, following the same procedure for above mentioned standard metal, ten pieces of bonded-metals bonded under the bonding temperature of 1300° C. and ten pieces of bonded-metals bonded under the bonding temperature of 1150° C. were prepared. Next, under the condition of hiding history of respective bonded-metals, each intensity of ultrasonic wave reflected by the bonding interface 4 was measured. Then the bonded-metals were classified into two groups: ones having an intensity of a noise-echo level and the other ones having intensity over a noise-echo level.

Next, only for the bonded-metals determined that an intensity of an ultrasonic wave reflected by the interface 4 were noise-echo level, 100% inspection were performed as follows: the attenuation of an ultrasonic wave through the bonding interface 4 was measured by employing a rectangular transducer having a side of 10 mm and causing a longitudinal wave having a frequency of 5 MHz to generate so that an angle of refraction might be 20°. Then the bonding temperature of the bonded-metal were estimated. The acceptance criteria was defined as −10 dB: the bonded-metals having a relative specific intensity −10 dB or more (corresponding to the bonding temperature below or equal to 1200° C.) were defined as unacceptable based on the expression (1) . By the 100% inspection, the bonded-metal bonded under a temperature of 1300° C. were all detected.

Next, the measured attenuation of the ultrasonic wave were substituted for the expression (2), thereby obtaining each tensile strength. The tensile strength of the bonded-metal bonded under a bonding temperature of 1300° C. was 826 MPa, and that bonded under a bonding temperature of 1150° C. was 328 MPa. Further, test specimens were sampled from the selected steel pipes bonded under bonding temperatures of 1300° C. and 1150° C. respectively, then each tensile strength being measured. The results were 835 MPa and 360 MPa, respectively, being in good agreement with the estimation based on the expression (2).

These results indicates that if the step of detecting deficiency is carried out prior to measuring an attenuation amount of an ultrasonic wave through a bonding interface, then estimation of a bonding property achieves high accuracy.

As described above, the preferred embodiment is not limited to above mentioned preferred embodiment. For example, referring to above mentioned preferred embodiment, the step of detecting deficiency is firstly performed, then the step of measuring an attenuation amount is performed. Alternatively, the step of detecting deficiency and the step of measuring an attenuation amount may be performed simultaneously.

By only one scanning, an intensity of reflected wave and an attenuation amount of an ultrasonic wave through an interface can be measured simultaneously. This simultaneous measurement enables the scanning time to decrease by one-half times as short as that of the individual measurement.

In addition, the present invention is applied to the bonded-metal such as steel pipes. Alternatively, the present invention may be applied to bonded-metal such as plate, rod and the like. Further, in the preferred embodiment, the present invention is applied to metals bonded by a liquid diffusion bonding, which is made from duplex stainless steel with insertion of Ni based alloy foil. Alternatively, the present invention may be applied to the duplex stainless steel pipes bonded by a solid-state diffusion bonding, a fusion welding or a pressure welding, thereby the same advantage as the preferred embodiment can be achieved.

Further, metal to be bonded is not limited to duplex stainless steel or precipitation hardening stainless steel applying duplex stainless steel as the base metal. Alternatively, the present invention may be applied for such bonded-metal made from such material that attenuation of an ultrasonic wave largely varies due to variation of a bonding condition.

For example, since pearlite has a banded structure formed by ferrite and cementite, for which an attenuation amount of an ultrasonic wave becomes large. Martensite or an intermediate structure, however, for which an attenuation amount of an ultrasonic wave tends to become small. Therefore, a bonding property can be presented in terms of variation of an attenuation amount of an ultrasonic wave, thereby enabling to estimate a bonding property for following cases: martensite is produced by quenching and then bonding pieces of steel containing pearlite together, or pearlite is produced by cooling slowly a bonding zone and then bonding pieces of steel containing martensite or banded structure together.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method for examining bonded-metal by ultrasonic examination, the method comprising:

measuring an attenuation amount of an ultrasonic wave, said ultrasonic wave being generated by a sending probe and received by a receiving probe through a diffusion bonding interface, said sending probe and said receiving probe being disposed on the bonded-metal with putting said diffusion bonding interface therebetween, said bonded-metal being bonded by diffusion bonding under unknown condition; and examining a bonding property of said bonded-metal based on said attenuation amount, with utilizing a relationship between a bonding property and an attenuation amount for standard metal bonded under known condition measured preliminarily, and wherein said bonding property is a bonding temperature.

2. A method for examining bonded-metal by ultrasonic examination, the method comprising:

measuring an attenuation amount of an ultrasonic wave, said ultrasonic wave being generated by a sending probe and received by a receiving probe through a diffusion bonding interface, said sending probe and said receiving probe being disposed on the bonded-metal with putting said diffusion bonding interface therebetween, said bonded-metal being bonded by diffusion bonding under unknown condition; and examining a bonding property of said bonded-metal based on said attenuation amount, with utilizing a relationship between a bonding property and an attenuation amount for standard metal bonded under known condition measured preliminarily, and wherein said ultrasonic wave is of a longitudinal wave mode which is generated so that an angle of incidence to said bonded-metal may be within a range from 17° to 30° in the case of measuring said attenuation amount.

3. A method for examining bonded-metal by ultrasonic examination, the method comprising:

measuring an attenuation amount of an ultrasonic wave, said ultrasonic wave being generated by a sending probe and received by a receiving probe through a diffusion bonding interface, said sending probe and said receiving probe being disposed on the bonded-metal with putting said diffusion bonding interface therebetween, said bonded-metal being bonded by diffusion bonding under unknown condition; and examining a bonding property of said bonded-metal based on said attenuation amount, with utilizing a relationship between a bonding property and an attenuation amount for standard metal bonded under known condition measured preliminarily, and wherein said probes having each side within a range from 8 mm to 15 mm long.

4. A method for examining bonded-metal by ultrasonic examination, the method comprising:

detecting whether deficiency exist at a diffusion bonding interface or not, based on an intensity of reflected ultrasonic wave, said intensity being measured at the time of being received, said ultrasonic wave being generated by a sending probe and received by a receiving probe, said sending probe and said receiving probe being disposed on the bonded-metal so as to be the same side with respect to said diffusion bonding interface, said bonded-metal being bonded by diffusion bonding under unknown condition;

measuring an attenuation amount of an ultrasonic wave only for such bonded-metal detected that there is no deficiency, said ultrasonic wave being generated by a sending probe and received by a receiving probe through said diffusion bonding interface, said sending probe and said receiving probe being disposed on said bonded-metal with putting said diffusion bonding interface therebetween; and examining a bonding property of said bonded-metal based on said attenuation amount, with utilizing a relationship between a bonding property and an attenuation amount for standard metal bonded under known condition measured preliminarily, and wherein said bonding property is a bonding temperature.

5. A method for examining bonded-metal by ultrasonic examination, detecting whether deficiency exist at a diffsion bonding interface or not, based on an intensity of reflected ultrasonic wave, said intensity being measured at the time of being received, said ultrasonic wave being generated by a sending probe and received by a receiving probe, said sending probe and said receiving probe being disposed on the bonded-metal so as to be the same side with respect to said diffusion bonding interface, said bonded-metal being bonded by diffusion bonding under unknown condition;

measuring an attenuation amount of an ultrasonic wave only for such bonded-metal detected that there is no deficiency, said ultrasonic wave being generated by a sending probe and received by a receiving probe through said diffusion bonding interface, said sending probe and said receiving probe being disposed on said bonded-metal with putting said diffsion bonding interface therebetween; and examining a bonding property of said bonded-metal based on said attenuation amount, with utilizing a relationship between a bonding property and an attenuation amount for standard metal bonded under known condition measured preliminarily, and wherein said ultrasonic wave is of a transverse wave mode in the case of measuring said intensity, and said ultrasonic wave is of a longitudinal wave mode having frequency within a range of 4 MHz to 10 MHz generated so that an angle of incidence to said bonded-metal may be within a range from 17° to 30° in the case of measuring said attenuation amount.

6. A method for examining bonded-metal by ultrasonic examination, the method comprising:

detecting whether deficiency exist at a diffusion bonding interface or not, based on intensity of reflected ultrasonic wave, said intensity being measured at the time of being received, said ultrasonic wave being generated by a sending probe and received by a receiving probe, said sending probe and said receiving probe being disposed on the bonded-metal so as to be the same side with respect to said diffusion bonding interface, said bonded-metal being bonded by diffusion bonding under unknown condition;

measuring an attenuation amount of an ultrasonic wave, said ultrasonic wave being generated by a sending probe and received by a receiving probe through said diffusion bonding interface, said sending probe and said receiving probe being disposed on said bonded-metal with putting said diffusion bonding interface therebetween; and examining a bonding property of said bonded-metal based on said attenuation amount, with utilizing a relationship between a bonding property and an attenuation amount for standard metal bonded under known condition measured preliminarily;

whereby said detection and said measurement being performed simultaneously, and wherein said bonding property is a bonding temperature.

7. A method for examining bonded-metal by ultrasonic examination, the method comprising:

detecting whether deficiency exist at a diffusion bonding interface or not, based on an intensity of reflected ultrasonic wave, said intensity being measured at the time of being received, said ultrasonic wave being generated by a sending probe and received by a receiving probe, said sending probe and said receiving probe being disposed on the bonded-metal so as to be the same side with respect to said diffusion bonding interface, said bonded-metal being bonded by diffusion bonding under unknown condition;

measuring an attenuation amount of an ultrasonic wave, said ultrasonic wave being generated by a sending probe and received by a receiving probe through said diffusion bonding interface, said sending probe and said receiving probe being disposed on said bonded-metal with putting said diffusion bonding interface therebetween; and examining a bonding property of said bonded-metal based on said attenuation amount, with utilizing a relationship between a bonding property and an attenuation amount for standard metal bonded under known condition measured preliminarily;

whereby said detection and said measurement being performed simultaneously, and wherein said ultrasonic wave is of a transverse wave mode in the case of measuring said intensity, and said ultrasonic wave is of a longitudinal wave mode having frequency within a range of 4 MHz to 10 MHz generated so hat an angle of incidence to said bonded-metal may be within a range from 17° to 30° in the case of measuring said attenuation amount.

8. A method for examining bonded-metal by ultrasonic examination, the method comprising:

detecting whether deficiency exist at a diffusion bonding interface or not, based on an intensity of reflected ultrasonic wave, said intensity being measured at the time of being received, said ultrasonic wave being generated by a sending probe and received by a receiving probe, said sending probe and said receiving probe being disposed on the bonded-metal so as to be the same side with respect to said diffusion bonding interface, said bonded-metal being bonded by diffusion bonding under unknown condition;

measuring an attenuation amount of an ultrasonic wave, said ultrasonic wave being generated by a sending probe and received by a receiving probe through said diffusion bonding interface, said sending probe and said receiving probe being disposed on said bonded-metal with putting said diffusion bonding interface therebetween; and examining a bonding property of said bonded-metal based on said attenuation amount, with utilizing a relationship between a bonding property and an attenuation amount for standard metal bonded under known condition measured preliminarily;

whereby said detection and said measurement being performed simultaneously, and wherein said probes having each side within a range from 8 mm to 15 mm long.

9. A method for examining bonded-metal by ultrasonic examination, the method comprising:

detecting whether deficiency exist at a diffusion bonding interface or not, based on an intensity of reflected ultrasonic wave, said intensity being measured at the time of being received, said ultrasonic wave being generated by a sending probe and received by a receiving probe, said sending probe and said receiving probe being disposed on the bonded-metal so as to be the same side with respect to said diffusion bonding interface, said bonded-metal being bonded by diffusion bonding under unknown condition;

measuring an attenuation amount of an ultrasonic wave only for such bonded-metal detected that there is no deficiency, said ultrasonic wave being generated by a sending probe and received by a receiving probe through said diffusion bonding interface, said sending probe and said receiving probe being disposed on said bonded-metal with putting said diffusion bonding interface therebetween; and examining a bonding property of said bonded-metal based on said attenuation amount, with utilizing a relationship between a bonding property and an attenuation amount for standard metal bonded under known condition measured preliminarily, and wherein said probes are rectangular probes having each side within a range from 8 mm to 15 mm long.

* * * * *